(12) United States Patent
Wright et al.

(10) Patent No.: US 8,541,027 B2
(45) Date of Patent: *Sep. 24, 2013

(54) FIXATION DEVICES FOR TISSUE REPAIR (75) Inventors: Emma Jayne Wright, York (GB); James William Huckle, Northallerton (GB); Saad Aboul Majeed Ali, York (GB)

(73) Assignee: Smith & Nephew, Inc., Memphis, TN (US)

( * ) Notice: Subject to any disclaimer, the term of this patent is extended or adjusted under 35 U.S.C. 154(b) by 1135 days.

This patent is subject to a terminal disclaimer.

(21) Appl. No.: 10/479,746

(22) PCT Filed: May 31, 2002

(86) PCT No.: PCT/GB02/02602
§ 371 (c)(1),
(2), (4) Date: Aug. 9, 2004

(87) PCT Pub. No.: WO02/098475
PCT Pub. Date: Dec. 12, 2002

(65) Prior Publication Data
US 2004/0265282 A1    Dec. 30, 2004

(30) Foreign Application Priority Data
Jun. 6, 2001 (GB) .................................. 0113697.7

(51) Int. Cl.
*A61K 9/14* (2006.01)
(52) U.S. Cl.
USPC ...................................................... 424/484
(58) Field of Classification Search
None
See application file for complete search history.

(56) References Cited

U.S. PATENT DOCUMENTS

| | | | |
|---|---|---|---|
| 3,225,766 A * | 12/1965 | Baptist et al. ................. | 606/230 |
| 4,353,996 A | 10/1982 | Marconi et al. | |
| 4,933,178 A | 6/1990 | Capelli | |
| 4,952,404 A | 8/1990 | Valee et al. | |
| 5,104,398 A | 4/1992 | Planck et al. | |
| 5,137,734 A | 8/1992 | Spiegelman et al. | |
| 5,270,300 A | 12/1993 | Hunziker | |
| 5,461,139 A | 10/1995 | Gonda et al. | |
| 5,609,609 A | 3/1997 | Ohshima et al. | |
| 5,609,629 A | 3/1997 | Fearnot et al. | |
| 5,854,382 A | 12/1998 | Loomis | |
| 5,858,365 A * | 1/1999 | Faller ......................... | 424/184.1 |
| 5,916,585 A * | 6/1999 | Cook et al. ................... | 424/426 |
| 6,152,141 A * | 11/2000 | Stevens et al. ................ | 128/898 |
| 6,153,252 A * | 11/2000 | Hossainy et al. .............. | 427/2.3 |
| 6,206,883 B1 | 3/2001 | Tunc | |
| 6,224,630 B1 | 5/2001 | Bao et al. | |
| 6,261,585 B1 | 7/2001 | Sefton et al. | |
| 6,316,522 B1 | 11/2001 | Loomis et al. | |
| 6,403,758 B1 | 6/2002 | Loomis | |
| 6,596,296 B1 | 7/2003 | Nelson et al. | |
| 6,881,766 B2 | 4/2005 | Hain | |
| 6,991,804 B2 | 1/2006 | Helmus et al. | |
| 7,033,603 B2 | 4/2006 | Nelson et al. | |
| 7,056,523 B1 | 6/2006 | Claude et al. | |
| 7,279,175 B2 | 10/2007 | Chen et al. | |
| 2001/0047202 A1 | 11/2001 | Slaikeu et al. | |
| 2003/0040809 A1 | 2/2003 | Goldmann et al. | |
| 2003/0158598 A1 | 8/2003 | Ashton et al. | |
| 2003/0229390 A1 | 12/2003 | Ashton et al. | |
| 2004/0054104 A1 | 3/2004 | Pacetti | |
| 2004/0162580 A1 | 8/2004 | Hain | |
| 2004/0193257 A1 | 9/2004 | Wu et al. | |
| 2004/0236416 A1 | 11/2004 | Falotico | |
| 2004/0265282 A1 | 12/2004 | Wright et al. | |
| 2006/0193769 A1 | 8/2006 | Nelson et al. | |
| 2006/0233887 A1 | 10/2006 | Day | |
| 2006/0286289 A1 | 12/2006 | Prajapati et al. | |
| 2006/0287675 A1 | 12/2006 | Prajapati et al. | |
| 2006/0287676 A1 | 12/2006 | Prajapati et al. | |
| 2007/0016251 A1 | 1/2007 | Roby | |
| 2007/0134292 A1 | 6/2007 | Suokas et al. | |
| 2007/0207189 A1 | 9/2007 | Belcheva et al. | |

FOREIGN PATENT DOCUMENTS

| | | |
|---|---|---|
| CN | 1389270 | 8/2003 |
| EP | 0 295 721 B1 | 1/1992 |
| EP | 1743659 A1 | 1/2007 |
| JP | H380868 | 4/1991 |
| JP | 3080868 | 5/1991 |
| JP | 10-305105 | 11/1998 |
| WO | WO 90/11071 | 10/1990 |
| WO | WO 97/47254 | 12/1997 |
| WO | WO 98/58690 | 12/1998 |
| WO | WO 99/29251 * | 6/1999 |

(Continued)

OTHER PUBLICATIONS

Lins et al. Scand. J. Thor. Cardiovasc. Surg. 22:34-45; 1998.*

(Continued)

*Primary Examiner* — Michael Burkhart
(74) *Attorney, Agent, or Firm* — Norman F. Hainer, Jr.

(57) ABSTRACT

Fixation devices for tissue repair, for example sutures, surgical arrows, staples, darts, bolts, screws, buttons, anchors, nails, rivets or barbed devices comprise at least one of angiogenic material; angiogenic precursor material which is capable of breaking down in vivo to form angiogenic material; and tissue-engineered material, which tissue-engineered material is capable of producing angiogenic material. In a preferred form the material is incorporated into a polymer matrix having predetermined hydrophobicity to allow controlled release of angiogenic materials such as butyric or hydroxybutyric acid or salts thereof. Polymer matrix compositions comprising angiogenic materials and methods for tissue repair are also provided.

4 Claims, 4 Drawing Sheets

(56) References Cited

FOREIGN PATENT DOCUMENTS

| WO | WO 99/53943 | | 10/1999 |
|---|---|---|---|
| WO | WO 01/21211 | * | 3/2001 |
| WO | WO02098475 A1 | | 12/2002 |
| WO | WO03064531 A1 | | 8/2003 |
| WO | WO2005025449 A2 | | 3/2005 |
| WO | WO2006116000 A2 | | 11/2006 |

OTHER PUBLICATIONS

Modulation of angiogenesis-related proteins synthesis by sodium butyrate in colon cancer cell line HT29, Carcinogenesis, vol. 23, No. 5, pp. 735-740, 2002.

First Office Action regarding Japanese Patent Application No. 2009-266561 mailed Aug. 1, 2012.

Dobson De et al, 1-Butyryl-glycerol; a novel angiogenesis factor secreted by differentiating adipocytes., Cell., Apr. 20, 1990, 61(2), 223-30.

Office Action mailed Feb. 12, 2013, in corresponding Japanese Application No. 2009-266561.

Covidien TI-CRON information brochure, p. 2; www.covidien.com/imageServer.aspx?contentID=14369&contenttype=application/pdf—last accessed Nov. 21, 2011.

Yonekura K et al., "UFT and Its Metabolites Inhibit the Angiogenesis Induced by Murine Renal Cell Carcinoma, as Determined by a Dorsal Air Sac Assay in Mice," Clinical Cancer Research, Aug. 1999.

* cited by examiner

FIXATION DEVICES FOR TISSUE REPAIR

The invention is concerned with the provision of fixation devices that improve tissue repair and with the use of such devices in medical treatment. In particular the invention is concerned with the fixation of tissues, which have limited or no vascular supply, such as meniscal cartilage, articular cartilage, ligament, bone and ischaemic tissue and where angiogenesis is desirable or a prerequisite for good tissue repair.

A wide variety of fixation devices exist for use in invasive medical treatments. These devices may be used to rejoin, re-affix, hold or otherwise partake in the repair of tissue during and after surgery and other medical treatments.

An aim of medical practitioners following surgery, for example, is to incite rapid healing and tissue repair throughout the treatment site. A factor in the promotion of tissue repair is the extent to which reparative cells and other factors can permeate through to the tissue in question. This, in turn, is dependent upon the extent to which blood vessels can form in and around the site.

The formation of new blood vessels from pre-existing ones is known as angiogenesis. Angiogenesis is an essential process during development of the human body—particularly embryonic development. Development of the human embryo commences with fusion of blood islands into vascular structures in the process of vasculogenesis; subsequently angiogenesis begins, with new vessels sprouting off from the vessels formed during vasculogenesis. Angiogenesis normally tails off, however, when the body becomes adult: with the exception of the female reproductive system, angiogenesis in the adult mainly occurs during tissue repair after wounding or inflammation, although it is also associated with adult pathological conditions, such as tumour growth, rheumatoid arthritis, psoriasis and diabetes.

The principle cell type involved in angiogenesis is the microvascular endothelial cell. Following injury and/or in response to angiogenic factors the basement membrane of endothelial cells in the parent blood vessel is degraded, a process mediated by endothelial cell proteases. Once the basement membrane is degraded, endothelial cells migrate out into the perivascular space. Cells at the base of the sprout proliferate and replace the migrated cells. A new basement membrane is then formed and two contiguous sprouts fuse together to form a loop. Subsequently a lumen forms and blood begins to flow.

The endothelial cell is the central cell type involved in angiogenesis because it is capable of expressing all the necessary information for the formation of new microvascular networks. It appears to achieve this by acting in concert with many different cell types to form new vessels. While not wishing to be bound by any theory, these other cell types may promote angiogenesis by expressing growth factors and cytokines that stimulate the proliferation and migration of the primary cellular components of the vascular wall, including endothelial cells.

Therapeutic angiogenesis is the clinical use of angiogenic factors or, in some cases, genes encoding these factors to enhance or promote the development of blood vessels in ischaemic/avascular tissue. The ideal agent for therapeutic angiogenesis would be safe, effective, inexpensive and easy to administer.

It would also be highly desirable to provide angiogenic factors in a controlled way over a predetermined period of time Angiogenic factors are known from the following prior documents: WO 90/11075, EP 0 295 721 and WO 99/53943.

It is an aim of the present invention to provide medical devices, which release angiogenic factors that promote blood vessel formation in the surrounding tissue.

It is a further aim of the present invention to provide fixation devices which promote tissue repair in the surrounding tissue and which will release factors that promote blood vessel vaso-dilation Thus according to one aspect of the invention there is provided a fixation device for tissue repair comprising at least one of angiogenic material; angiogenic precursor material which is capable of breaking down in vivo to form angiogenic material; and tissue-engineered material, which tissue-engineered material is capable of producing angiogenic material.

In a first embodiment of this aspect of the invention, the fixation device comprises tissue-engineered material, which tissue-engineered material is capable of producing angiogenic material.

In a second embodiment of this aspect of the invention the material forming the device may be at least partially bioresorbable.

As used herein, the term "angiogenic material" is to be understood to include not only material comprising one or more angiogenic factors but also materials which stimulate blood supply by inducing vaso-dilation of pre-existing vascular material.

As used herein, the term "angiogenic factor" is to be understood to include materials, which directly or indirectly promote angiogenesis, for example, materials that are capable of breaking down in vivo to form angiogenic material As used herein, the term "angiogenesis" is to be understood to include the growth of new blood vessels from existing ones.

As stated above, the angiogenic material comprises one or more angiogenic factors.

A first class of angiogenic factor, which falls within the scope of the invention, comprises angiogenic peptide growth factors, including autologous, allogenic, xenogenic, recombinant and synthetic forms of these. This class includes the vascular endothelial growth factor family, particularly VEGF121, 165, 189 and 206; fibroblast growth factor family, particularly FGF-1, FGF-2, FGF-7 (keratinocyte growth factor); transforming growth factor family (TGF-α, -β; platelet derived growth factor, particularly PDGF-AA, PDGF-B and PDGF-AB; platelet derived endothelial cell growth factor (PD-ECGF); hypoxia inducible factor-1 (HIF-1); scatter factor (SF, also known as hepatocyte growth factor or HGF); placenta growth factor (PlGF)-1, -2; tumour necrosis factor α (TNF-α); midkine; pleiotrophin; insulin-like growth factor-1; epidermal growth factor (EGF); endothelial cell growth factor (ECGF); endothelial stimulating angiogenic factor (ESAF); connective tissue growth factor (CTGF); CYR61; Angiogenin; Angiotrophin.

A second class of angiogenic factors which falls within the scope of the invention comprises blood clot breakdown products, such as thrombin and heparin including autologous, allogeneic, xenogeneic, recombinant and synthetic forms of these materials.

A third class of angiogenic factors which falls within the scope of the invention comprises those based around butyric acid, including:
  butyric acid (butanoic acid, $C_4H_8O_2$) and butyric acid salts, including sodium, potassium, calcium, ammonium and lithium salts
  butyric acid derivatives and polymers containing butyric acid residues
  α-monobutyrin (1-glycerol butyrate; 1-(2,3 dihydroxypropyl) butanoate; $C_7H_{14}O_4$)

α-dibutyrin (1,3-glyceroldibutyrate; 1,3-(2 hydroxypropyl)dibutanoate; $C_{11}H_{20}O_5$)
β-dibutyrin (1,2-glyceroldibutyrate; 1,2-(3 hydroxypropyl)dibutanoate; $C_{11}H_{20}O_5$)
tributyrin (glycerpl tributyrate; 1,2,3-propyl)tributanoate; $C_{15}H_{26}O_6$)
hydroxybutyrate and polymers containing hydroxybutyric acid residues.

The compounds disclosed in WO 90/11075 are also expressly included in the scope of the present invention. These have general formula:

wherein X is O, NH, S or $CH_2$, and $R^1$ is alkyl or acyl of 2-10C which is saturated or unsaturated and which is unsubstituted or substituted with one or more substituents which do not interfere with angiogenic activity, said substituents selected from the group consisting of OH, OR, SH, SR, $NH_2$, NHR, $NR_2$ and halo wherein each R is independently lower alkyl (1-4C); and each $R^2$ and $R^3$ is independently H, $PO_3^{-2}$, or is alkyl or acyl as defined above, or in formula 1, $R^2$ and $R^3$ taken together are an alkylene moiety or $OR^2$ and $OR^3$ form an epoxide, which amount is effective to stimulate angiogenesis in said subject.

wherein $R^2$ and $R^3$ are acyl or H
wherein said acyl group is $CH_3(CH_2)_{n1}CO$, wherein n1 is an integer of 0-8; or is neopentoyl or cyclohexylcarbonyl
wherein, in the compound of formula 1, $R^2$ and $r^3$ taken together are wherein n2 is an integer of 0-7
the method stated above wherein one of $R^2$ and $R^3$ is H and the other is alkyl (1-10C)
the method stated above wherein X is O
the method stated above wherein $R^1$ is acyl (2-6C)

A fourth class of angiogenic factors, which falls within the scope of the invention, comprises inflammatory mediators. These materials promote tissue inflammation, which in turn promotes angiogenesis. Included in this class are tumour necrosis factor α (TNF-α); prostaglandins E1 and E2; interleukins 1, 6 and 8; nitric oxide.

Disparate other angiogenic factors are known which do not fall into any class. Included in this group are hyaluronan, para-thyroid hormone, angiopoietin 1, del-1, erythropoietin, fas (CD95), follistatin, macrophage migration inhibitory factor, monocyte chemoattractant protein-1, transferrin and nicotinamide.

The fixation devices of the invention aptly comprise angiogenic precursor material, which is capable of breaking down in vivo to form angiogenic material. Angiogenic precursor materials according to the invention include fibrin, including autologous, allogeneic, xenogeneic, recombinant and synthetic forms thereof, and hyaluronic acid. Preferably, the angiogenic precursor material is fibrin; degradation fragments of fibrin found to have advantageous angiogenic properties include fragments D and E.

Alternatively, the fixation devices of the invention may comprise tissue-engineered material, which tissue-engineered material is capable of producing angiogenic material. Tissue-engineered material falling within the scope of the invention includes material capable of producing angiogenic material comprising angiogenic factors contained within the first class of angiogenic factors (see above). Tissue-engineered material according to the invention includes proprietary products such as DEPMAGRAFT™ and TRANSCYTE™.

Advantageously, the angiogenic material is present in an amount that is therapeutically effective for the mammalian organism in question. Preferably, the angiogenic material is present in an amount that is therapeutically effective for humans. As used herein, the term "therapeutically effective amount" is to be understood to mean sufficient to cause or increase the rate of angiogenesis. What constitutes a therapeutically effective amount is specific to the angiogenic factor(s) comprised within the angiogenic material. In the case of VEGF and FGF-2, for example, the fixation device should comprise up to 50 μg of factor per mg of device, preferably less than 25 μg/mg.

The term "fixation device" includes any devices used to rejoin, re-affix, hold or otherwise partake in the repair of tissue. A non-exhaustive list of such devices includes sutures, surgical arrows, staples, darts, bolts, screws, buttons, anchors, nails, rivets or barbed devices. The fixation devices of the invention also include augmentation devices such as cuffs which are used to promote angiogenisis at the interface of different tissue types such as ligament and bone or tendon and muscle.

There follow ways of incorporating the angiogenic material into or onto devices according to the invention:

The fixation devices according to the invention may be impregnated with angiogenic material after manufacture of the fixation device. Impregnation may result in angiogenic material being distributed throughout up to the whole of the fixation device. Distribution of the angiogenic material may be homogenous or inhomogenous. In the latter case, the fixation device would comprise localised regions comprising higher concentrations of angiogenic material. Preferably, impregnation results in angiogenic material being present in at least a region extending into the device from at least one of its external surfaces. More preferably, impregnation results in angiogenic material being distributed throughout the whole of the fixation device. Whether the angiogenic material is distributed homogenously or inhomogenously throughout the device and, if inhomogenously, what form the distribution profile has, will depend on the effects to be achieved. In particular, the distribution profile will strongly influence the release profile of angiogenic material into the surrounding tissue.

Impregnation methods, which may be used according to the invention, include dipping, soaking, under vacuum, if appropriate.

In a second embodiment, the angiogenic factor, material or precursor therefore may be physically incorporated into the main fabric of the fixation device. Aptly, therefore, the angiogenic material will constitute discrete zones within the fabric of the fixation device. Suitably, threads or filaments of angiogenic material may be co-spun or woven together with fibrous or filamentary material comprising the main fabric of the fixation device. For example, threads of angiogenic material may be braided with polyethylene terephthalate fibres used to produce a suture. Alternatively, the angiogenic material may be co-extruded with the main fabric material of the fixation device.

In a third embodiment, the angiogenic material may be coated either directly onto at least one of the external surfaces of the fixation device after manufacture of the fixation device or, alternatively incorporated into a carrier, from which it can be controllable released, and the thus formed mixture coated directly onto the fixation device.

Preferably, where the angiogenic factors, materials at precursors are coated onto or formed as discrete components or zones within the fixation device they may be first formulated with a hydrophobic polymer to be delivered under controlled release conditions by a diffusion mechanism from the monolithic matrix comprising the factor and hydrophobic polymer. Thus, for example, by incorporating a water miscible or soluble angiogenic material into a polymer matrix, which is hydrophobic in nature, the release rate of the angiogenic material can be controlled. Water is required to solubilise the material, thereby subsequently releasing the material. The degree of hydrophobicity of the polymer matrix controls the rate of water permeation, and hence the rate of release of the angiogenic material.

Suitably, the angiogenic material may be blended with a polymer comprising vinyl acetate residues.

Ethylene-vinyl acetate (EVA) copolymers are preferred hydrophobic matrix polymers, which can be used for the preparation of formulations for the controlled release of angiogenic factors.

Altering the vinyl acetate content of the EVA polymers will affect the hydrophobicity of the polymer, and therefore modify the release rate of the angiogenic factor. Decreasing the vinyl acetate content of the carrier matrix will increase the hydrophobic and crystalline nature of the polymer, resulting in a less porous polymer and thus a slower rate of release Fabrication parameters such as copolymer composition (matrix hydrophobicity), angiogenic factor loading and matrix coating (slowing release by encapsulating ethylene-vinyl acetate/angiogenic factor matrix) can be modified to alter the release characteristics of the angiogenic factor.

Although the EVA copolymer formulations may used with any angiogenic material having appropriate water solubility or miscibility, Preferred formulations comprise butyric acid in an EVA copolymer matrix.

Although the use of butyric acid (or salts thereof) an angiogenic material, its use is believed not been demonstrated hitherto. There are two possible reasons for this. The first is that butyric acid has a particularly pungent smell and is unpleasant to use. The second reason is the finding that butyric acid is to rapidly biodegraded that it is unable to effectively promote angiogenisis before it is broken down to ineffective metabolites.

We have found that by formulating butyric acid or water soluble/miscible salts thereof with ethylene-vinyl acetate, the noted disadvantages are avoided. The angiogenic material can be delivered at a controlled dosage rate in amounts, which are not malodorous.

Hydroxybutyric acid and derivatives, salts and polymers thereof, the butyrin derivatives such as monobutyrin and may also be formulated with polymers containing pre-determined amounts of hydrophobic residues Thus in accordance with another aspect of the invention there is provided a composition of matter comprising a blend of an ethylene-vinyl acetate copolymer and a water-soluble or water miscible angiogenic material or precursor therefor in a therapeutically effective amount sufficient to promote angiogenisis.

Preferably the composition of matter comprises a blend of an ethylene-vinyl acetate copolymer matrix and butyric acid or a water-soluble or water miscible salt thereof in a therapeutically effective amount sufficient to promote angiogenisis.

Water-soluble or water miscible derivatives of butyric or hydroxy butyric acid which are suitable for the compositions of matter of the invention include the sodium, potassium, calcium, ammonium and lithium salts.

Ethylene vinyl acetate copolymers will suitably be admixed or bended with up to 15% by weight, more suitably up to 10% by weight, of the angiogenic material.

The ethylene-vinyl acetate copolymers comprising the polymer matrix are known materials and may be prepared by conventional methods known per se. The vinyl acetate content of the copolymer may aptly range from 5 to 50% by weight of the copolymer, depending on the desired rate of release of the angiogenic factor. Suitably vinyl acetate contents range from about 8% to about 40% by weight. More suitably vinyl acetate contents up to about 35% by weight will provide sustained release of therapeutically effective amounts of angiogenic factor.

In vitro studies have shown that compositions containing about 10% by weight angiogenic factor with an ethylene-vinyl acetate copolymer, having vinyl acetate contents within the range or 8 to 35% by weight, should release the angiogenic factor, specifically butyric acid, within the therapeutic range of 1-450 μg/ml per $cm^3$ per day for up to 21 days.

EVA copolymers containing the angiogenic factor can be used as a coating for any fixation device.

The angiogenic material may be coated onto all external surfaces of the fixation device. Coating methods, which may be employed, include dip coating and spray coating. Preferably, the fixation device is dip-coated with angiogenic material.

The present invention further provides a method for the repair of damaged tissue comprising the step of implanting a device in accordance with the invention into a tissue defect.

Preferably, the tissue into which the fixation device is implanted is avascular tissue. More preferably, the tissue is meniscal cartilage, articular cartilage, ligament, bone or ischaemic tissue. The fixation devices of the invention may be used at the interface of different tissue types, for example between ligament and bone or between muscle and tendon.

EXAMPLE 1

O Ti-Cron™ braided sutures, which are non-resorbable and should therefore have no significant effect on angiogenesis, were impregnated with either butyric acid or monobutyrin. The butyric acid impregnated sutures gave a release rate in the range of 25-3000 ng per cm of suture, or 25-300 ng butyric acid per 1.4 mg of suture per day for 21 days. The sutures were impregnated by soaking them for at least 7 days in a stock solution of butyric acid. The monobutyrin impregnated sutures gave a release rate in the range of 25-3000 ng per cm of suture, or 25-3000 ng monobutyrin per 1.4 mg of suture per day for 7 days. Prior to the surgery the sutures were removed from the stock solution and wiped twice with a surgical swab.

Blue Faced Leicester Cross Suffolk Tubs were employed for this example. This is a fairly robust species of sheep with large long bones. Anatomically sheep bones closely approximate to those of man and are regularly used as models for bone graft substitutes and healing.

The surgical procedure to implant the suture involved the meniscus being accessed by a standard medial arthrotomy. Using a scalpel, an 8 mm full thickness longitudinal tear was created in the red-white zone of one of the medial menisci.

The tear was then sutured using (i) a 0 Ti-Cron suture which had been impregnated with butyric acid, as detailed above, or (ii) a 0 Ti-Cron suture which had been impregnated with monobutyrin, as detailed above, or (iii) a control untreated 0 Ti-Cron suture which did not contain butyric acid or monobutyrin. The suture technique used was an outside-in horizontal mattress suture. Joints were then closed and the animals allowed to recover.

The animals were permitted to put weight on the joints immediately thereafter and were terminated at the 6 week time point.

Figure 1:
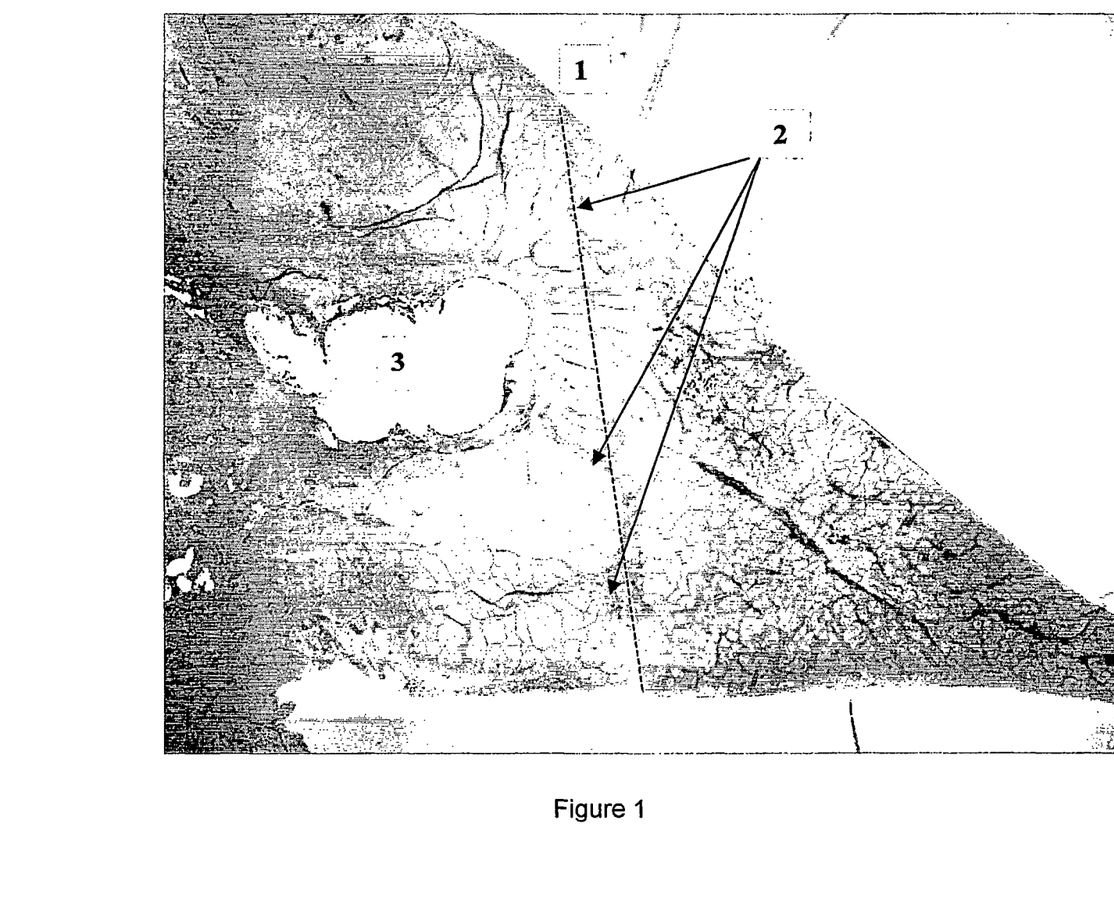
FIG. 1 illustrates a tear in the red-white zone of meniscal cartilage.

FIG. 1 of the accompanying drawings illustrates a tear, which cuts through the red-white zone of meniscal cartilage, made as described supra. FIG. 1 shows a haematoxylin and phloxine stained histological section, the repaired tear is roughly indicated by dotted line (1), this is a red-white tear. The suture can be seen in the section (3). Angiogenesis (2) in the form of migrating endothelial cells and newly formed blood vessels can be observed as can healing of the tear.

It is the form taken by the angiogenesis which is the best indicator of the success of this experiment: as discussed above, angiogenesis is the formation of new blood vessels from existing ones. This means that angiogenesis could only be observed radiating out from existing blood vessels in the red zone and in fact what is observed is a steady front of new blood vessels (2) advancing from the red zone through the transitional zone towards the white zone.

Figure 2:
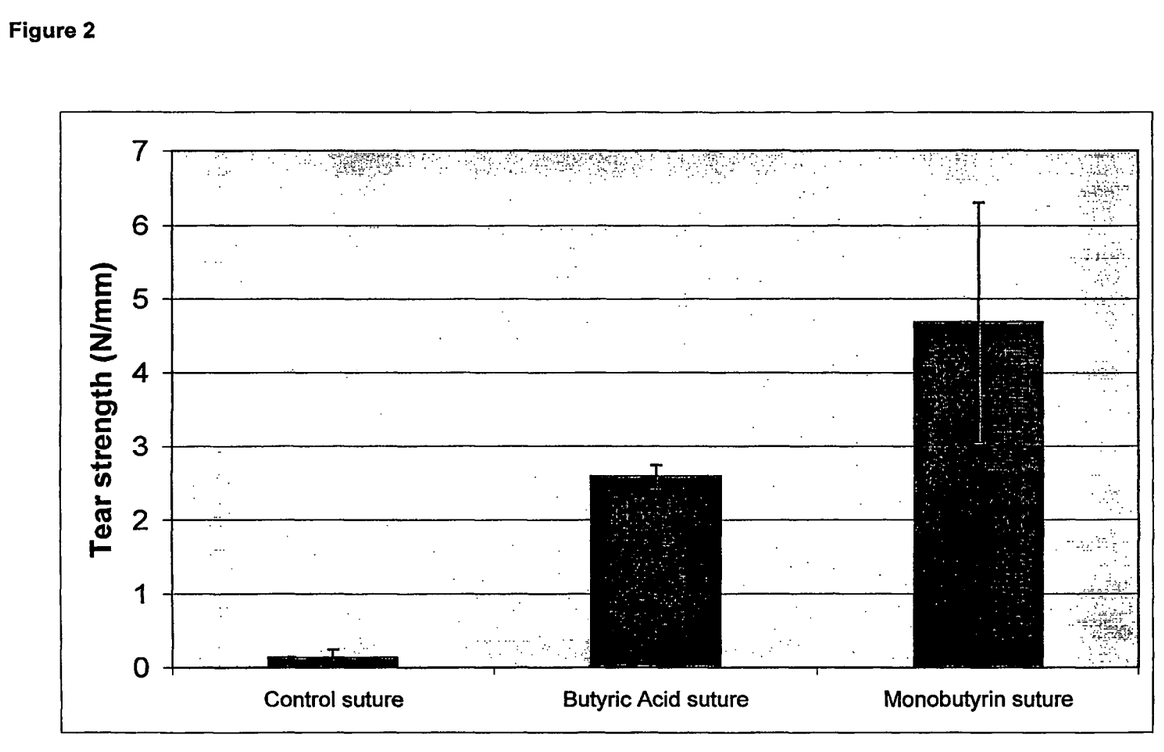
FIG. 2 shows the results of a biomechanical evaluation performed on menisci treated with control sutures and sutures of the present invention.

With reference to FIG. 2, biomechanical evaluation was performed on treated menisci biopsied after 6 weeks in-vivo. The test was based on experiments performed by Roeddecker et al. (1994) which involved circumferentially tearing menisci and measuring average tear loads and average tear energies of the repaired areas.

Initially, an incision of approximately 5-10 mm was made in the posterior horn of each meniscus to produce two "free ends". This incision was positioned to align with, and meet, the repaired area of meniscus. Fully repaired areas of meniscus were sometimes hard to identify, so the incision was positioned according to best judgement. The sutures used to initiate the repair were exposed at the periphery of the meniscus and the suture knots were removed.

Testing was performed using the Instron 5566 materials test machine. The "free ends" of each meniscus were gripped using pincer grips and a 100N capacity load cell was used to measure the resultant tear load throughout the test. Once complete, the average tear load, from the force/displacement curve, was identified using two cursors and the tear energies under this same area of the force/displacement curves were automatically calculated.

Three control menisci were tested, where the repairs were initiated with untreated suture, three were tested where the suture had been impregnated with butyric acid and three were tested where the suture had been impregnated with monobutyrin.

The sutures impregnated with an angiogenic factor substantially increased the strength of the repair tissue above that of the untreated control. Normal meniscal tissue has a tear strength of 14N/mm.

EXAMPLE 2

Sodium butyrate was loaded into three EVA copolymers, with differing vinyl acetate contents, and the release rate of butyric acid into Phosphate Buffer Solution (PBS) determined.

Thus, sodium butyrate (10% by weight) was compounded into three EVA copolymers, respectively containing 8, 18 and 28% by weight of vinyl acetate residues. Thin films of the compounded samples were produced by compression moulding and 12 mm disks (0.06 mm thick) were cut from each film and placed in 2 ml of PBS. The PBS was replaced on a daily basis for up to seven days and then at 2, 3 and 4-week timepoints. The isolated PBS extracts were analysed for butyric acid content using a HPLC method.

Figure 3:
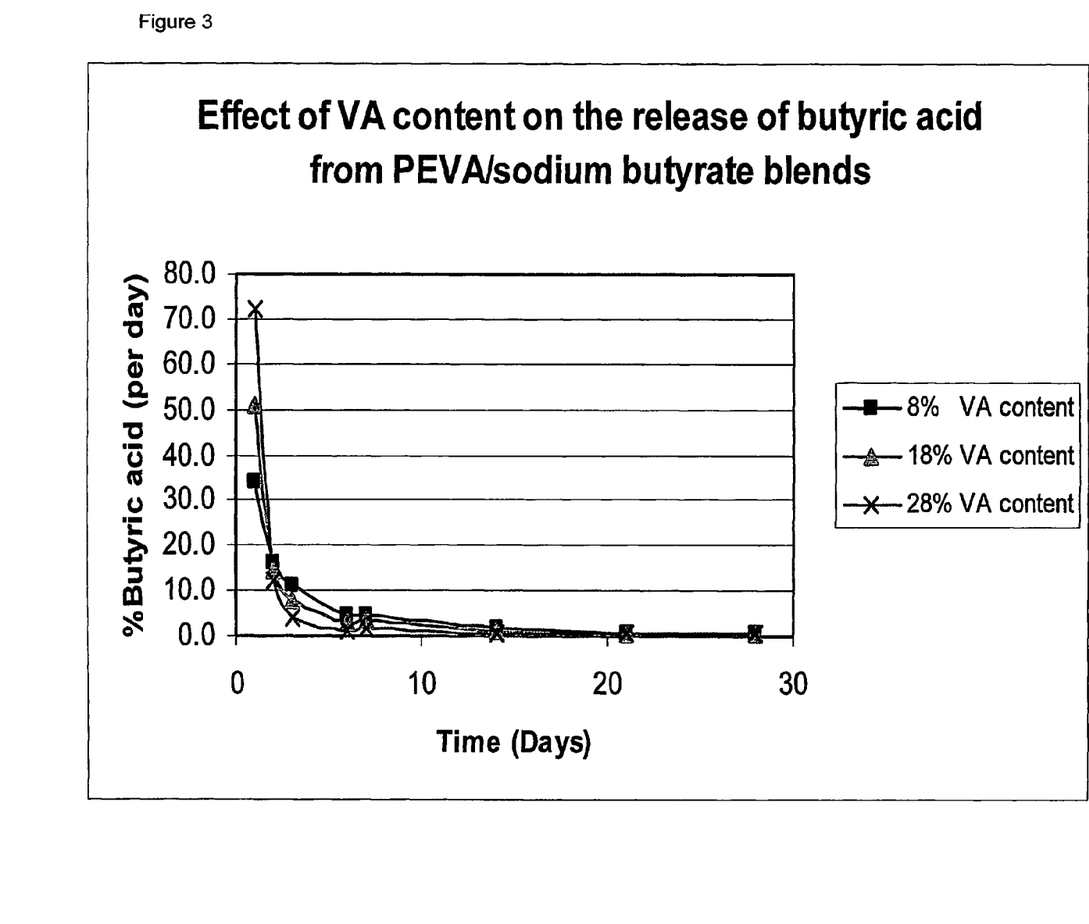
FIG. 3 shows the effect of vinyl-acetate content on the release of butyric acid from polyethylene vinyl acetate (PEVA)/sodium butyrate blends.

FIG. 3 clearly shows that modifying the vinyl acetate content of the polymer does control the release of the butyric acid.

EXAMPLE 3

Figure 4:
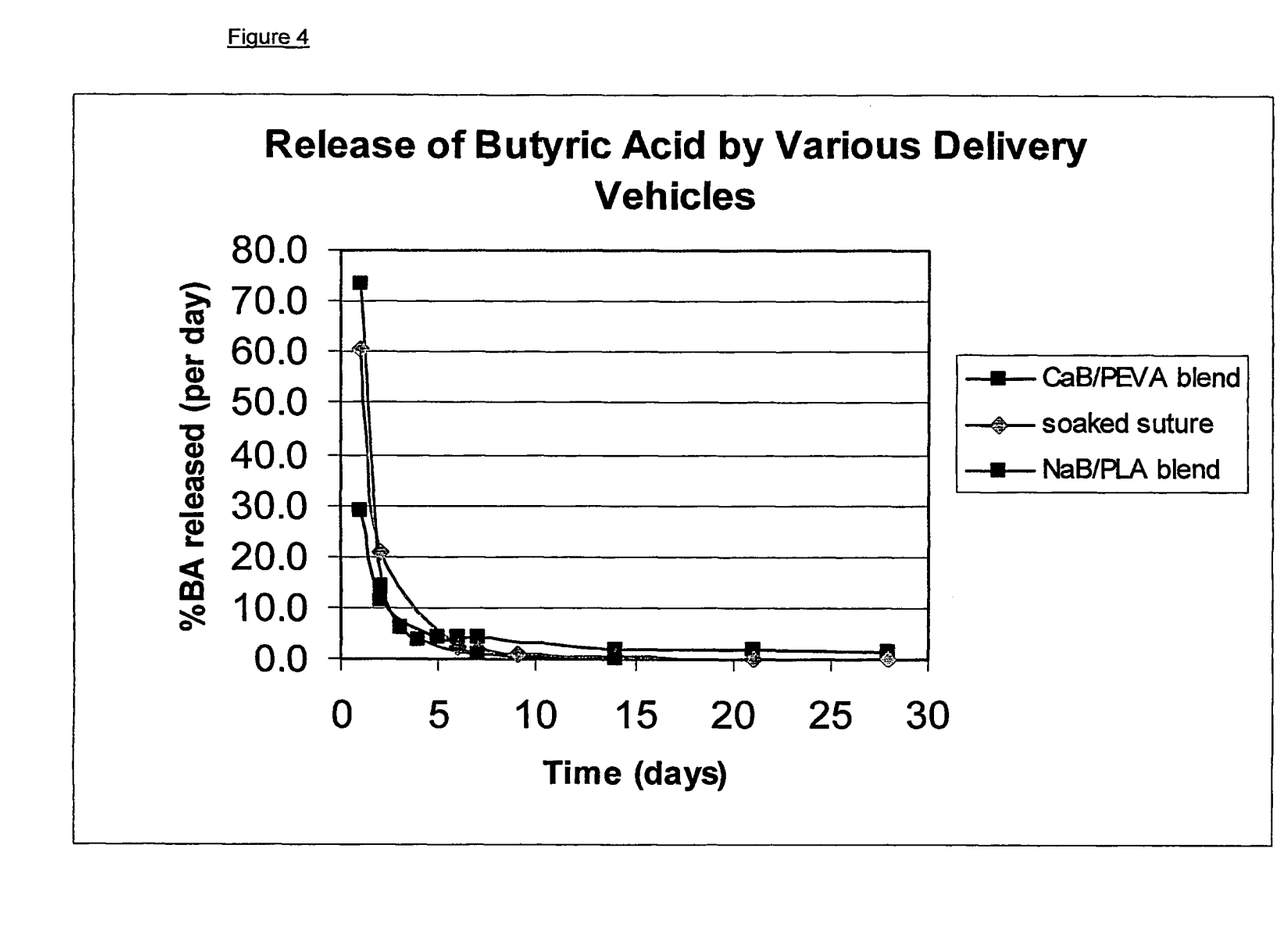
FIG. 4 shows the release of butyric acid by various delivery vehicles.

Butyric acid and salts thereof were formulated with different polymer compositions and the rate of release into PBS determined EXAMPLE 3a Sutures made from 0 Ti-Cron were soaked in solutions of butyric acid (50,000 μg cm$^{-3}$). After 66 h, the sutures were removed from the butyric acid solution and placed in 2 ml of PBS. The PBS was replaced on a daily basis for up to seven days and then at 2, and 3-week timepoints. The isolated PBS extracts were analysed for butyric acid content using a HPLC method. Over 90% of the butyric acid was released within the first four days (FIG. 4).

EXAMPLE 3b

Sodium butyrate (1% w/w) was compounded into poly (L) lactic acid (PLLA) and then rods of the polymer extruded. The release rate of butyric acid form these rods was evaluated as described above. Butyric acid was released rapidly from the PLLA into PBS.

EXAMPLE 3c

Calcium butyrate (1% w/w) was compounded into an ethylene-vinyl acetate copolymer (33% by weight vinyl acetate content) and then rods of the polymer extruded. The release rate of butyric acid form these rods was evaluated as described above.

Thus it can be seen that by altering the hydrophobicity of the polymer can control the release rate of an angiogenic factor.

The invention claimed is:
1. A fixation device for tissue repair comprising a water soluble or water miscible angiogenic material or precursor thereof in admixture with a non-absorbable hydrophobic polymer, wherein the angiogenic material is sodium butyrate.

2. The fixation device according to claim 1 wherein the polymer includes up to about 15% by weight of the angiogenic material.

3. The fixation device according to claim 1 wherein the fixation device comprises a suture, a surgical arrow, a staple, a dart, a bolt, a screw, a button, an anchor, a nail or rivet, or a barbed surgical device.

4. A fixation device for tissue repair consisting of a water-soluble or water miscible angiogenic material or precursor thereof in admixture with a non-absorbable hydrophobic polymer, wherein the angiogenic material is sodium butyrate.

* * * * *